United States Patent [19]

Jung et al.

[11] 4,256,913
[45] Mar. 17, 1981

[54] PREPARATION OF CARBOXYLIC ACIDS USING A BF$_3$ CATALYST COMPLEX

[75] Inventors: John A. Jung, East Hanover, N.J.; Jimmy Peress, West Haven, Conn.

[73] Assignee: Chem Systems Inc., New York, N.Y.

[21] Appl. No.: 28,460

[22] Filed: Apr. 9, 1979

[51] Int. Cl.$^3$ .................. C07C 51/14; C07C 51/377; C07C 53/122; C07C 53/124
[52] U.S. Cl. ..................... 562/521; 203/66; 560/214; 560/233; 562/599; 568/697
[58] Field of Search .............. 560/233, 214; 562/521, 562/599; 260/410.9 R, 413

[56] References Cited

U.S. PATENT DOCUMENTS

| | | | |
|---|---|---|---|
| 2,135,459 | 11/1938 | Loder et al. | 562/521 |
| 2,378,009 | 6/1945 | Hanford et al. | 560/233 |
| 2,967,873 | 1/1961 | Koch et al. | 560/233 |
| 3,349,107 | 10/1967 | Pawlenko | 560/233 |

OTHER PUBLICATIONS

Pawlenko, Chemie. Ing. Techn., 40, 52 (1968).
Moller, Bernstoff–Chemie., 45, 129 (1964).

*Primary Examiner*—Vivian Garner
*Attorney, Agent, or Firm*—Bert J. Lewen

[57] ABSTRACT

Propylene and ethylene may be carbonylated to form carboxylic acid esters or carboxylic acids in the presence of a catalyst complex containing 1 mole of BF$_3$ and 1 mole of a second complexing component. The carboxylic acid product or acid portion of the ester product has one more carbon atom than the olefin reacted. High yields of these products are obtained. In the case of the formation of the ester, the second complexing component is an alcohol, while in the case of the preparation of carboxylic acid, the second complexing component is water. Methyl isobutyrate and methyl propionate formed by the carbonylation of propylene and ethylene, respectively, in the presence of a BF$_3$.CH$_3$OH catalyst may be dehydrogenated to prepare methyl methacrylate and methyl acrylate, respectively. Similarly, the isobutyric acid and propionic acid formed from propylene and ethylene, respectively, in the presence of BF$_3$.H$_2$O catalyst may be dehydrogenated to prepare methacrylic acid and acrylic acid, respectively.

5 Claims, No Drawings

PREPARATION OF CARBOXYLIC ACIDS USING A BF₃ CATALYST COMPLEX

BACKGROUND OF THE INVENTION

It has long been desired to find an inexpensive means of making alkyl methacrylate and alkyl acrylates, basic monomers for the formation of acrylic resins, as well as acrylic and methacrylic acids. Conventionally, methyl methacrylate is prepared by reacting acetone and hydrogen cyanide to form cyanohydrin; dehydrating the cyanohydrin in the presence of sulfuric acid to form methacrylamide sulfate; and finally reacting the sulfate with methanol and sulfuric acid to form the desired methyl methacrylate. Because of the high cost of the raw materials and the need to dispose of by-product ammonium sulfate, this process is deficient.

Other proposed processes for making methyl methacrylate and methacrylic acid involve isobutylene oxidation, ammoxidation, epoxide formation and t-butanol oxidation. These processes also suffer from high capital costs and, in some cases, raw material costs.

In the present invention it is proposed to prepare acrylic acid, methacrylic acid and corresponding esters from olefins and carbon monoxide in the presence of a catalyst complex composed of one mole of $BF_3$ and one mole of either water or an alcohol, as the case may be. Where the alcohol is methanol and the olefin propylene, the product is methyl isobutyrate. The latter may be dehydrogenated to prepare the methyl methacrylate. In this process the end products are formed from readily available raw materials, no by-products are formed, and capital costs are economically attractive.

In the past it has been proposed that methacrylic acid (or methyl isobutyrate) be prepared from propylene by reacting propylene with carbon monoxide and water (or methanol) and a number of catalysts have been claimed to effect this reaction. For example, U.S. Pat. No. 3,579,511 describes the reaction of olefins with carbon monoxide and water in the presence of catalyst compositions essentially comprising iridium compounds and complexes together with an iodide promoter. Similarly German OLS No. 2,739,096 describes the carbonylation of propylene in the presence of palladium salts. Unfortunately, the use of noble metals as catalyst is costly and this aspect makes these approaches economically unattractive.

Carbonylation of higher olefins, i.e., isobutylene and above, with carbon monoxide and water in the presence of acid catalyst has long been known. The reaction, known as the Koch synthesis, has been commercialized by Exxon [Hydrocarbon Processing 44, 139 (1965)] and also described in French Pat. No. 1,252,675 granted to Shell International. A variety of acid catalysts are described including sulfuric and phosphoric acid and hydrated boron trifluoride. The Exxon process uses boron trifluoride dihydrate and the French patent prefers a mixture of phosphoric acid and boron trifluoride. In both instances the feed used was isobutylene and the product was primarily 2,2-dimethyl propionic acid. Only in the case of high molecular weight olefins, particularly those branched at the double bond, was it believed that one could form carboxylic acids having only one more carbon than the olefin. This was predicated on the finding that, in order to obtain high conversions, the less reactive lower olefins, i.e., ethylene and propylene, could only be carbonylated under severe reaction conditions, and that under these conditions the major reaction was the polymerization of the olefin.

Pawlenko in Chemie Ing. Techn. 40, 52 (1968) and German Pat. No. 1,226,557 amply supports the above observations. After recognizing that under the original conditions of the Koch synthesis ethylene and propylene cannot be carbonylated and that under severe conditions in the presence of boron trifluoride hydrate, ethylene forms the high molecular weight ethyl ester of alpha-methyl-alpha-ethylbutyric acid, Pawlenko proposes the use of a $[H_3O][BF_4]$ catalyst. With this catalyst, he reports that ethylene and propylene under comparatively mild conditions form primarily carboxylic acids having over seven carbon atoms. Similarly, using $[CH_3OH][BF_3]$ as the catalyst, methyl esters of $C_6$, $C_8$ and $C_{12}$ acid were obtained.

For the above reason, much of the prior art relating to the Koch synthesis is limited to higher olefin feeds. See, for example, U.S. Pat. No. 3,349,107; Izv. Akad. Nauk., SSSR Ser. Khim. 1970 (2) 424; Ibid. 1970 (7) 1673; and Ibid. 1972 (2) 428.

In the foregoing prior art, while boron trifluorides are generally described, most of the work with the higher olefins used such complexes wherein the number of moles of water or alcohol present is two or more times the number of moles of the boron trifluoride. See, for example, the above-cited Hydrocarbon Processing article and the three USSR references. In Moller, Brennstoff-Chemie, 45, 129 (1964), it is noted that all mixtures of $BF_3$ hydrate catalyst may be used which contain more water than $BF_3.H_2O$ up to 2 moles of water for each mole of $BF_3$. A similar stipulation is made for the methanol complex. The catalyst $BF_3.CH_3OH$ is only said to be useful for certain cyclic olefins with the added observation that such catalyst is of little interest because it cannot be recovered in a useable form. Furthermore, this reference, too, is limited to the carbonylation of higher olefins, $C_5$ to $C_{12}$.

BRIEF SUMMARY OF THE INVENTION

This invention relates to a method of preparing low molecular weight saturated carboxylic acids and esters thereof from lower olefins, particularly ethylene and propylene, by carbonylation with carbon monoxide and a catalyst complex of $BF_3$ and a second component. The second component is water where the end product is a carboxylic acid, and an alcohol where the end product is a carboxylic acid ester.

The active catalyst complex is formed by the addition of one mole of $BF_3$ to one mole of the second component. The reaction takes place in the liquid catalyst solution through which gaseous carbon monoxide and the olefin are passed. The reaction conditions are moderate and a high yield of the acid or the ester, as the case may be, is obtained. The acid product or the carboxylic acid portion of the ester product has one more carbon atom than the initial olefin. Substantially no polymerization of the olefin occurs.

The saturated carboxylic acid ester product may be readily dehydrogenated to form an unsaturated carboxylic acid ester, e.g., methyl isobutyrate obtained from the carbonylation of propylene may be dehydrogenated to form methyl methacrylate.

Alternatively, the propylene may be carbonylated to form isobutyric acid which may thereafter be dehydrogenated to methacrylic acid.

DETAILED DESCRIPTION OF THE INVENTION

In the present invention, gaseous feedstocks consisting of either propylene or ethylene and carbon monoxide are used. The olefins may be obtained from any source, most generally from steam cracking of hydrocarbons.

The carbon monoxide employed should have a purity of at least 99%, though mixtures of carbon monoxide and other inert gases, such as carbon dioxide, may be used.

It is preferred that the olefin and carbon monoxide be of high purity since this will simplify product recovery and minimize losses in purge streams required to remove inerts from the reaction system.

The reaction may be carried out at temperatures of from 0° C. to 100° C., preferably from 20° C. to 60° C. The temperatures should be kept at moderate levels throughout the process because high temperatures could result in the formation of by-products, especially heavier esters.

In the carbonylation reaction of the invention, one mole of carbon monoxide reacts with each mole of olefin. This is known as the external reactant ratio. On the other hand, it is desirable to maintain a large molar excess of carbon monoxide in the vapor phase in order to suppress undesirable side reactions. This ratio (known as the internal carbon monoxide to olefin molar ratio) is controlled by the system pressure, degree of agitation, and purge rate and is broadly at least 5:1, preferably at least 8:1. As a practical matter, ratios of not more than 1000:1, preferably not more than 100:1, are used.

In view of the foregoing, it will be understood that in a batchwise process and during the start-up of a continuous process a large molar excess of the carbon monoxide is fed. However, in the continuous process, once steady state conditions are achieved, only about one mole of carbon monoxide is fed to the reactor for each mole of olefin.

The reaction pressure, while not critical, is generally of from 10 to 300 atmospheres, most preferably from 30 to 100. While higher pressures are not detrimental and in some instances actually favor selectivity to the desired products, again practical considerations such as equipment design and safety factors favor the use of the pressure ranges set forth above.

The selection of the appropriate catalyst complex is an essential feature of the invention. As pointed out previously, in the prior art the most commonly used catalyst complex contains one mole of $BF_3$ for each two moles of water or alcohol. In contrast, the catalyst complex used in the instant invention contains equal molar amounts of $BF_3$ and the water or alcohol (hereinafter the "second component"). These catalysts are stable complexes having specific physical properties. They exist as liquids at room temperature and therefore can be conveniently used as the reaction solvent.

While it is understood that the 1:1 molar ratio catalyst is the active constituent in the instant invention, the catalyt may be prepared using ratios of from about 0.75 to 10 moles of $BF_3$ for each mole of the second component, preferably from 0.75 to 2 moles per mole. It will be understood that, when less than one mole of the $BF_3$ is utilized with, say, methanol, the catalyst is a mixture of $BF_3.CH_3OH$ and $BF_3.2CH_3OH$. This latter compound is also a stable complex; however, in contrast to the 1:1 molar ratio catalyst, it is non-selective to the desired product and of relatively low activity. Accordingly, a substantial amount of such complex is undesirable.

On the other hand, where the molar ratio is in excess of 1:1, the 1:1 catalyst complex (e.g., $BF_3.CH_3OH$) is in admixture with uncomplexed $BF_3$. Since excess $BF_3$ is not catalytically active for the desired acid or ester, sizeable excesses are of little advantage.

As noted above, in performing the process of the invention it is advantageous to use the catalyst as the reaction medium. Other organic constituents may be present, so long as they do not interfere with the carbonylation. The reaction period is not critical, but should be selected so as to achieve acceptable conversions without unduly lengthening the process cycle. As a practical matter, the reaction period ranges from about 10 minutes to 3 hours.

Wherein the end product sought to be obtained is the carboxylic acid, the second component is water. On the other hand, wherein the carboxylic acid ester is sought, the second component is an alcohol. Generally, the lower alkyl alcohols having from 1 to 4 carbon atoms are preferred. These include methanol, ethanol, propanol, isopropanol and n-butanol and its isomers. Additionally, other alcohols can be used. These include alkyl alcohols having from 5 to 12 carbon atoms and aralkyl alcohols such as benzyl alcohol, alpha-phenethyl alcohol and beta-phenethyl alcohol.

In addition, it has been found that other catalyst additives such as hydrogen fluoride, sulphuric acid, and phosphoric acid, are not necessary for the synthesis of the desired products.

The products of the carbonylation may be dehydrogenated by several known procedures such as described in Japan Kokai No. 78 82,720 or Japan Pat. No. 73 19,614 where these carbonylation products (methyl isobutyrate or isobutyric acid) are oxidatively dehydrogenated at 300° C. and 1 atm. pressure with oxygen-containing gases over catalysts composed of mixed metal oxides, the major component being molybenum oxide. In U.S. Pat. No. 3,721,705, isobutyric acid or methyl isobutyrate is oxidatively dehydrogenated at 500° C. in the presence of sulfur. In British Pat. No. 1,141,625, a dehydrogenation is carried out without added oxidizing agents over alumina catalysts at 600° C. and reduced pressure.

To illustrate more fully the instant invention, attention is directed toward the following examples:

EXAMPLE 1

To a 600 ml. stirred autoclave at 20° C. is added 100 g. of a $BF_3.CH_3OH$ catalyst. A 9:1 carbon monoxide/propylene mixture is added to the autoclave at 60 atm. The mixture is heated in the autoclave at 50° C. and held at this temperature for one hour. A sample taken from the autoclave is analyzed by gas-liquid chromatography. All of the propylene is converted and the selectivity to methyl isobutyrate is 94%.

The autoclave is cooled, depressurized, and then repressurized again to 60 atm. with the 9:1 gas mixture. This procedure is repeated several times until about 50% of the methanol in the catalyst reacts. The mixture remaining in the autoclave is again analyzed and found to be approximately a 2:1:1 mixture of $BF_3$/methanol/methyl isobutyrate (about 38 wt. % methyl isobutyrate). The selectivity to the methyl isobutyrate is 88%. The foregoing solution is introduced into a distillation apparatus.

In order to recover the methyl isobutyrate, the foregoing solution is distilled at 60° C. at 50 mm Hg to remove the $BF_3$. This leaves in the distillation flask a solution containing a $BF_3$/methanol/methyl isobutyrate complex in a molar ratio of 1:1:1. Sufficient methanol is added to convert the solution to a 1:4:1 molar ratio. The resulting solution is distilled at a temperature of 40°–80° C. and a pressure of 0.1–1.0 atm. to recover a methyl isobutyrate/methanol azeotrope as an overhead fraction. Hexane is added to the methyl isobutyrate/methanol solution and a low boiling azeotrope of methanol and hexane is distilled overhead. The residue is methyl isobutyrate. A technique for recovering and recycling the catalyst is the subject matter of assignee's copending patent application U.S. Ser. No. 28,459, filed simultaneously with this application and entitled "Recovery of Carbonylation Catalyst Complex".

The methyl isobutyrate thus obtained in dehydrogenated to form methyl methacrylate in accordance with the following procedure:

Methyl isobutyrate, oxygen, steam and nitrogen in a molar ratio of 3:4:4:89 are fed into a reactor containing a catalyst consisting of molybdenum, vanadium and phosphorous oxides in an atomic ratio of Mo:V:P of 12:2:1. The temperature is maintained at 300° C. with a residence time of 1 second. Under these conditions 90% of the feed methyl isobutyrate is converted to methyl methacrylate and methacrylic acid with a combined selectivity of 75%. The methacrylic acid is then esterified to methyl methacrylate.

EXAMPLE 2

In this example, 100 g. of a $BF_3.H_2O$ complex is added to a 600 ml. stirred autoclave and maintained at 20° C. A 9:1 carbon monoxide/propylene gas mixture is added at 60 atms. After addition of this mixture, the autoclave is heated to 50° C. and maintained at this temperature for one hour. The autoclave is cooled, depressurized and repressurized three times. Analysis by gas-liquid chromatography indicates that the autoclave contents consist of 25% by weight isobutyric acid. The selectivity to isobutyric acid is 98%.

EXAMPLE 3

In this example, 90 g. of a $BF_3.CH_3OH$ complex is added to a 600 ml. autoclave and maintained at 20° C. A 9:1 carbon monoxide/ethylene gas mixture is added at 68 atms. After addition of this mixture, the autoclave is heated to 50° C. and maintained at this temperature for three hours. The autoclave is cooled and depressurized. Analysis by gas-liquid chromatography indicates that the autoclave contents consist of 1 to 2% by weight methyl propionate plus 2 to 3% by weight of heavier materials. The selectivity to methyl propionate is about 25%. Under the conditions of the oxidative dehydrogenation described in Example 1, methyl propionate gives a combined selectivity of 75% to methyl acrylate and acrylic acid.

EXAMPLE 4

Under conditions similar to Example 3, except that $2BF_3.CH_3OH.H_2O$ is the catalyst, ethylene is carbonylated to produce propionic acid in 25% selectivity. Propionic acid is dehydrogenated in accordance with dehydrogenation conditions of Example 1 and gives acrylic acid in 80% selectivity.

EXAMPLE 5

Under the conditions of Example 1, except that $BF_3.i-C_3H_7OH$ is the catalyst, propylene is carbonylated to give isopropyl isobutyrate in 90% selectivity.

COMPARATIVE EXAMPLE I

The procedure of Example 1 is repeated, except that 100 g. of $BF_3.2C_3OH$ is employed. Only 10 to 20% of the propylene is converted in one hour. The only product produced is isopropyl methyl ether. This clearly shows the criticality of the ratio of the $BF_3$ to the second component of the catalyst.

Having thus described our invention, what we claim and desire to protect by Letters Patent is:

1. A process for the carbonylation of an olefin selected from the group consisting of ethylene and propylene which comprises: reacting said olefin with carbon monoxide in a liquid catalyst which is an equimolar amount of $BF_3$ and water at a temperature of from 0° C. to 100° C. and with an internal mole ratio of carbon monoxide to olefin of at least 5:1 until about 50% of the water is reacted, whereby the reaction product obtained is $BF_3$-water and a carboxylic acid containing one more carbon atom than the olefin employed in a molar ratio of approximately 2:1:1.

2. The process of claim 1 wherein the olefin is propylene, the catalyst is $BF_3.H_2O$ and the carboxylic acid obtained is isobutyric acid.

3. The process of claim 1 wherein the olefin is ethylene, the catalyst is $BF_3.H_2O$, and the carboxylic acid obtained is propionic acid.

4. The process of claim 1 wherein the liquid catalyst is $BF_3.H_2O$ which is formed by the reaction of from 0.75 to 2 moles of $BF_3$ with one mole of $H_2O$.

5. The process of claim 1 wherein the carbonylation reaction product is dehydrogenated to a corresponding unsaturated carboxylic acid.

* * * * *